United States Patent [19]
Lurie

[11] Patent Number: 6,029,667
[45] Date of Patent: *Feb. 29, 2000

[54] HEART FAILURE MASK AND METHODS FOR INCREASING NEGATIVE INTRATHORACIC PRESSURES

[75] Inventor: Keith G. Lurie, Minneapolis, Minn.

[73] Assignee: CPRX LLC, Minneapolis, Minn.

[ * ] Notice: This patent is subject to a terminal disclaimer.

[21] Appl. No.: 09/019,843

[22] Filed: Feb. 6, 1998

Related U.S. Application Data

[63] Continuation-in-part of application No. 08/747,371, Nov. 12, 1996, Pat. No. 5,730,122.

[51] Int. Cl.⁷ .......................... A61M 16/00; A62B 18/02; A62B 18/10
[52] U.S. Cl. .............. 128/207.16; 128/206.21; 128/205.25; 128/207.12
[58] Field of Search .............. 128/207.16, 207.12, 128/205.25, 206.21, 206.24, 206.28, 204.18

[56] References Cited

U.S. PATENT DOCUMENTS

| | | | |
|---|---|---|---|
| 3,815,606 | 6/1974 | Mazal | 128/351 |
| 4,077,404 | 3/1978 | Elam | 128/145.8 |
| 4,166,458 | 9/1979 | Harrigan | 128/24 R |
| 4,226,233 | 10/1980 | Kritzer | 128/205.13 |
| 4,259,951 | 4/1981 | Chernack et al. | 128/200.14 |
| 4,298,023 | 11/1981 | McGinnis | 137/529 |
| 4,316,458 | 2/1982 | Hammerton-Fraser | 128/205.24 |
| 4,446,864 | 5/1984 | Watson et al. | 128/207.14 |
| 4,449,526 | 5/1984 | Elam | 128/206.21 |
| 4,533,137 | 8/1985 | Sonne | 272/99 |
| 4,601,465 | 7/1986 | Roy | 272/99 |
| 4,881,527 | 11/1989 | Lerman | 128/30.2 |
| 5,109,840 | 5/1992 | Daleiden | 128/205.13 |
| 5,163,424 | 11/1992 | Kohnke | 128/205.13 |
| 5,193,544 | 3/1993 | Jaffe | 128/634 |
| 5,235,970 | 8/1993 | Augustine | 128/200.26 |
| 5,301,667 | 4/1994 | McGrail et al. | 128/205.14 |
| 5,355,879 | 10/1994 | Brain | 128/207.15 |
| 5,359,998 | 11/1994 | Lloyd | 128/203.11 |
| 5,392,774 | 2/1995 | Sato | 128/207.14 |
| 5,492,116 | 2/1996 | Scarberry et al. | 128/206.24 |
| 5,517,986 | 5/1996 | Starr et al. | 128/206.24 |
| 5,551,420 | 9/1996 | Lurie et al. | 128/205.13 |
| 5,692,498 | 12/1997 | Lurie et al. | 128/205.24 |
| 5,730,122 | 3/1998 | Lurie | 128/207.12 |

FOREIGN PATENT DOCUMENTS

| | | |
|---|---|---|
| 668771 | 8/1963 | Canada . |
| 2077608 | 3/1993 | Canada . |
| 0509773 | 10/1992 | European Pat. Off. . |
| 2139099 | 11/1984 | United Kingdom . |

OTHER PUBLICATIONS

Directions for Ambu® CardioPump™, pp. 1–8.
Cohen et al. (1992) "Active Compression–Decompression Resuscitation: A Novel Method of Cardiopulmonary Resuscitation" American Heart Journal 126 (5) : 1145–1150.
Cohen et al. (1992) "Active Compression–Decompression: A New Method of Cardiopulmonary Resuscitation" JAMA 267 (21) : 2916–2923.
Lindner et al. (1993) "Effects of Active Compression–Decompression Resuscitation on Myocardial and Cerebral Blood Flow in Pigs" Circulation 88 (3) : 1254–1263.

Primary Examiner—John G. Weiss
Assistant Examiner—Todd M. Martin
Attorney, Agent, or Firm—Townsend and Townsend and Crew LLP

[57] ABSTRACT

The invention provides methods and devices for treating a patient suffering from heart failure. According to one exemplary method, a facial mask is sealed around the patient's mouth and nose, with the mask including a one-way expiration valve and an inspiratory threshold valve. The threshold valve is biased to open when a threshold pressure within the mask is in the range from about −3 cm $H_2O$ to about −25 cm $H_2O$. With this arrangement, the patient breathes while the mask is sealed to the face, with the respiratory gasses being prevented from entering the patient's lungs during inhalation until the patient produces a pressure within the mask that is within the range from about −3 cm $H_2O$ to about −25 cm $H_2O$. At this point, the inspiratory valve opens to allow respiratory gasses into the lungs.

23 Claims, 4 Drawing Sheets

HEART FAILURE MASK AND METHODS FOR INCREASING NEGATIVE INTRATHORACIC PRESSURES

CROSS REFERENCE TO RELATED APPLICATIONS

This application is a continuation in part application of U.S. patent application Ser. No. 08/747,371, now U.S. Pat. No. 5,730,122 filed Nov. 12, 1996, the complete disclosure of which is herein incorporated by reference.

BACKGROUND OF THE INVENTION

The present invention relates generally to the field of cardiology, and more particularly to the field of heart failure. In this regard, the invention provides devices and methods that are useful in the treatment of congestive heart failure.

Heart failure is a condition which significantly affects millions of people throughout the world. Heart failure is the inability of the heart to pump blood at an adequate rate. Such a condition can result in, among others, congestion in the tissues, shortness and wheezing of breath, pitting edema, and an enlarged and tender liver. If not successfully treated, heart failure can be fatal.

For this reason, attempts to reduce or eliminate the symptoms of heart failure have been widespread. Some common methods for treating heart failure include drug therapies with diuretic agents, angiotensin converting enzyme inhibitors and digitalis. One particular method which has been found to be somewhat effective in reducing the symptoms of heart failure is to supply nitroglycerin to the heart. Supplemental oxygen has shown to be highly effective in severe heart failure. Such a treatment has shown to decrease right atrial, right ventricular, left atrial, and left ventricular pressures, especially during diastole, resulting in a greater aorta-left ventricular and diastolic gradient which in turn enhances overall myocardial perfusion.

Although the introduction of nitroglycerin into the heart has shown in some cases to be effective in reducing the symptoms of heart failure, such a treatment in many cases has limited effectiveness. For example, the administration of nitroglycerin usually requires physician supervision and can lead to a number of side effects including propound hypotension.

Hence, for these and other reasons it would be desirable to provide a way to decrease or eliminate the signs and symptoms of congestive heart failure which would be conducive with the normal lifestyle of a patient. Such a treatment should be both easy and convenient to use, be relatively inexpensive, and require little or no physician supervision.

SUMMARY OF THE INVENTION

The invention provides devices and methods which are useful in treating a patient suffering from heart failure. The methods of the invention provide a treatment by controlling the flow of respiratory gasses to the patient's lungs while the patient is actively or spontaneously breathing. In a broad sense, the treatment proceeds by preventing respiratory gasses from entering the patient's lungs during inhalation until a negative intrathoracic pressure that is in the range from about −3 cm $H_2O$ to about −25 cm $H_2O$, and more preferably from about −5 cm $H_2O$ to about −15 cm $H_2O$ is developed within the patient. At this point in time, respiratory gasses are allowed to flow into the lungs. Each time the patient inhales, this step is repeated to prevent respiratory gasses from entering the lungs until the specified negative intrathoracic pressure is developed within the patient. Optionally, when the patient exhales a slight increase in positive end expiratory pressure may be provided.

The methods of the invention may be performed while the patient breathes spontaneously or while assisted ventilation is be provided. Also, an assisted mechanical support may optionally be coupled to the patient during the treatment. For example, a body carass, iron lung device, vest or other device that alters the intrathoracic pressure, e.g., by transforming the vest into a bellows, may be applied to the patient's chest. In this way, the intrathoracic pressure may be increased and decreased during the treatment. Such a treatment is particularly useful with patients in an Intensive Care Unit.

In a specific method, the patient is treated by sealing a facial mask around the patient's mouth and nose, with the mask including a one-way expiration valve and an inspiratory threshold valve. The inspiratory threshold valve is biased to open when a threshold pressure within the mask is in the range from about −3 cm $H_2O$ to about −25 cm $H_2O$. While the mask is sealed to the patient's face, the patient spontaneously breathes, with respiratory gasses being prevented from entering into the patient's lungs during inhalation until the patient produces a pressure within the mask that is in the range from about −3 cm $H_2O$ to about −25 cm $H_2O$. At this point, the inspiratory valve opens to allow respiratory gasses to enter into the lungs. In this manner, no respiratory gasses are allowed to enter into the patient's lungs for a specified time which is dictated by the amount of time required to develop the specified negative intrathoracic pressure within the patient. In this way, both the magnitude and duration of negative intrathoracic pressure within the patient is greater than would otherwise exist if such a mask were not worn.

As an alternative to a facial mask, the method may employ the use of an endotracheal tube having a one-way expiration valve and an inspiratory threshold valve. The tube is placed in the patient's airway and functions in a manner similar to the facial mask. Such a device may find particular usefulness with severely ill patients in cardiogenic shock.

In one particular aspect of the method, respiratory gasses that are exhaled by the patient pass through the exhalation valve without substantial resistance. In this way, the patient may freely exhaust the gasses from his lungs without substantial impedance from the facial mask. In another aspect of the method, the seal between the facial mask and the patient's face is sufficient to maintain a pressure gradient between the pressure outside the mask and the pressure within the mask of at least +20 cm $H_2O$.

In a further aspect of the method, the mask may optionally include a port through which oxygenated gasses and/or medical therapies may be introduced directly into the interior of the facial mask. The mask may optionally also further include a backup inspiratory threshold valve which is biased to open when a threshold pressure within the mask is about 10% to about 100% greater than the threshold pressure of the other threshold valve. In this manner, if the primary threshold valve fails, the backup threshold valve will begin to operate to continue the treatment. Preferably, a whistle or other audible signal will be produced when the respiratory gasses begin to flow through the backup threshold valve.

In still a further aspect of the method, the mask may be sealed to the patient's face by strapping the mask around the patient's head. Optionally, an adhesive may be placed between the mask and the patient's face to provide an adequate seal.

The invention further provides an exemplary device for treating a patient suffering from heart failure. The device comprises a facial mask having a body and a seal which is employed to seal the body to the patient's face around the mouth and nose. The mask further includes a one-way expiration valve and an inspiratory threshold valve which is biased to open when a threshold pressure within the mask is in the range from about −3 cm $H_2O$ to about −25 cm $H_2O$.

The exhalation valve will preferably be configured to allow exhaled respiratory gasses to pass therethrough without substantial resistance. In another aspect, the seal on the mask will preferably be configured so that it will be sufficient to maintain a pressure gradient between the pressure outside the mask and the pressure within the mask of at least +20 cm $H_2O$.

The mask may optionally further include a backup inspiratory threshold valve which is biased to open when a threshold pressure within the mask is about 10% to about 100% greater than the threshold pressure of the other threshold valve.

The mask body is preferably constructed of a generally rigid material so that the mask will not inadvertently collapse, such as when a patient rolls over in bed. In yet another aspect, the mask may be provided with a strap for fastening the mask to the patient's head. Further, the seal may comprise an adhesive to secure the mask to the patient's face.

DESCRIPTION OF THE PREFERRED EMBODIMENT

Figure 1:
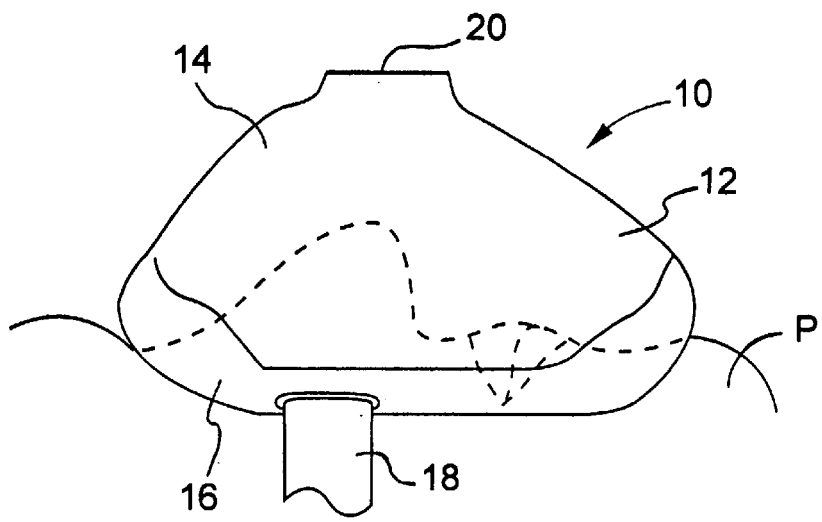
FIG. 1 is a side-view of an exemplary facial mask which may be employed to treat a patient suffering from heart failure according to the principles of the present invention.

The invention provides methods and devices which are particularly useful for the treatment of congestive heart failure. The methods and devices of the invention may also be useful in treating other conditions including, cardiogenic shock, hemorrhagic shock, certain kinds of syncope, cardiac arrest, and the like. According to the invention, a patient suffering from heart failure is treated by controlling the flow of respiratory gasses to the lungs during normal breathing by the patient. More particularly, the invention provides for the prevention of respiratory gasses from entering the patient's lungs until a negative intrathoracic pressure that is in the range from about −3 cm $H_2O$ to about −25 cm $H_2O$ and more preferably from about −5 cm $H_2O$ to about −15 $H_2O$ has developed within the patient. At this point in time, respiratory gasses are allowed to flow into the lungs. This procedure is preferably repeated each time the patient inhales so that respiratory gasses are prevented from entering the lungs for a specified amount of time during inhalation until the desired negative intrathoracic pressure is developed within the patient. The device can be used during periods of sleep and while the patient is awake. Typically, the device is used while the patient is breathing spontaneously. However, assisted ventilation can also be provided. Moreover, an assisted mechanical support may optionally be provided during the treatment. For example, a body carass, iron lung device, vest or other device that alters the intrathoracic pressure, e.g., by transforming the vest into a bellows, may be applied to the patient's chest. In this way, the intrathoracic pressure may be increased and decreased during the treatment.

The methods and devices of the invention are therefore useful in increasing both the duration and magnitude of negative intrathoracic pressure during normal breathing than would otherwise be experienced. When the intrathoracic pressure is lowered to a greater degree relative to atmospheric pressure, the pressures within the left ventricular cavity become more negative during periods of diastole. By lowering the left ventricular end diastolic pressure, the myocardial perfusion gradient is increased thereby reducing the signs and symptoms of heart failure.

The methods and devices of the invention will preferably employ a mechanical device that is included within a mask or endotracheal tube to prevent respiratory gasses from entering into the patient's airway until a desired negative intrathoracic pressure is developed within the patient. Such respiratory gasses will be preferably prevented from entering the patient's lungs while the patient is attempting to inhale. After the specified pressure range is obtained within the patient, air is allowed to freely flow into the lungs. Then, during exhalation, the exhaled respiratory gasses will preferably be allowed to exit the mask without substantial impedance. The use of such a mechanical device to produce the desired negative intrathoracic pressure is advantageous in that overall myocardial perfusion may be enhanced without a pharmacological means.

As previously described, respiratory gasses will preferably be prevented from entering the patient's lungs until the patient experiences a negative intrathoracic pressure that is within the range from about −3 cm $H_2O$ to about −25 cm $H_2O$, and more preferably from about −5 cm $H_2O$ to about −15 cm $H_2O$. It is believed that such a range is critical in producing the desired myocardial perfusion gradient which will lead to a reduction in the signs and symptoms of congestive heart failure. Intrathoracic pressures which exceed about −25 $H_2O$ will cause excessive work during respiration and the patient will tire easily and may lead to the development of negative pressure pulmonary edema.

Referring now to FIG. 1, an exemplary device 10 that is useful in treating a patient suffering from heart failure will be described. Device 10 comprises a facial mask 12 which is constructed of a mask body 14 and a seal 16. As shown, mask 12 is configured so that seal 16 will encompass the mouth and nose of a patient when placed over the patient's face.

Mask 12 is designed so that it may be conveniently worn by a patient at any time, but will be particularly useful when worn at night while sleeping, during emergencies, or when the patient is ambulating. As such, body 14 will preferably be constructed of a material which is sufficiently rigid to prevent the mask from collapsing if the patient were to roll over at night while asleep. Exemplary materials for constructing body 14 comprise a reinforced silicone seal, polyurethane, plastics, rubber, plexiglass, acrylics, other elastomeric materials which are preferably transparent, and the like.

Seal 16 will preferably be constructed of a material which is capable of forming a seal with the skin on the patient's face. Preferably, the seal will be adequate to prevent air from entering into the interior of the mask at the facial connection for pressures within the mask of at least about −25 cm $H_2O$ or greater. Preferable materials for constructing seal 16 comprise silicones, elastomeric materials, polyurethanes, rubber, and the like. Optionally, an adhesive may be placed between seal 16 and the patient's face to improve the seal. Another option for improving the seal between mask 12 and the patient's face is by providing a strap 18 which is placed around the patient's head to secure mask 12 to the patient's face.

Figure 2:
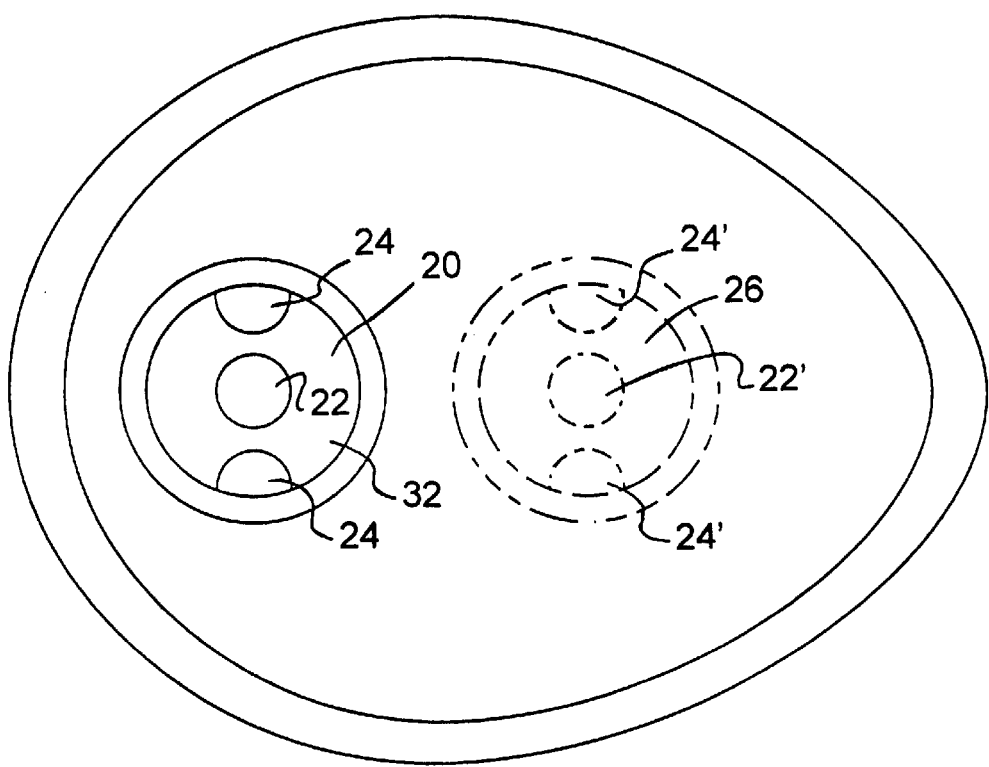
FIG. 2 is a top-view of the mask of FIG. 1.

Referring now to both FIGS. 1 and 2, device 10 further includes an airflow controller 20 which includes an inspiratory threshold valve 22 and a pair of exhalation valves 24, it being appreciated that only a single exhalation valve may be sufficient. As described in greater detail hereinafter, threshold valve 22 is employed to prevent respiratory gasses from flowing to the patient's lungs during inhalation until a specified negative intrathoracic pressure is developed within the patient. When such a pressure is obtained, threshold valve 22 opens to allow air to flow into the air interior of the mask. Exhalation valves 24 open freely upon exhalation of the patient to allow exhausted respiratory gasses to exit mask 12. As shown in FIG. 2, device 10 may further include a second or "backup" airflow controller 26 having an inspiratory threshold valve 22' and exhalation valves 24'. Controller 26 is essentially identical to airflow controller 20 except for the pressure range required to open the inspiratory threshold valve 22. More specifically, backup airflow controller 26 will preferably be configured so that inspiratory threshold valve 22' will open only in the event of the failure of threshold valve 22 of controller 20. Preferably, the inspiratory threshold 22' of backup controller 26 will be configured to open when a threshold pressure within the mask is about 10% to about 100% greater, and more preferably from about 20% to about 30% greater, than the threshold pressure of threshold valve 22 of controller 20. Optionally, backup controller 26 may include a whistle or other audio device to produce an audible signal when backup controller 26 becomes operational. In this way, the patient will be alerted when airflow controller 20 has failed and backup controller 26 has begun to operate.

Optionally, device 10 may include a port (not shown) which is formed within body 14 and allows for the delivery of oxygenated gasses and/or other medical therapies that may be introduced directly into the face mask and which may subsequently be inhaled by the patient.

Figure 3:
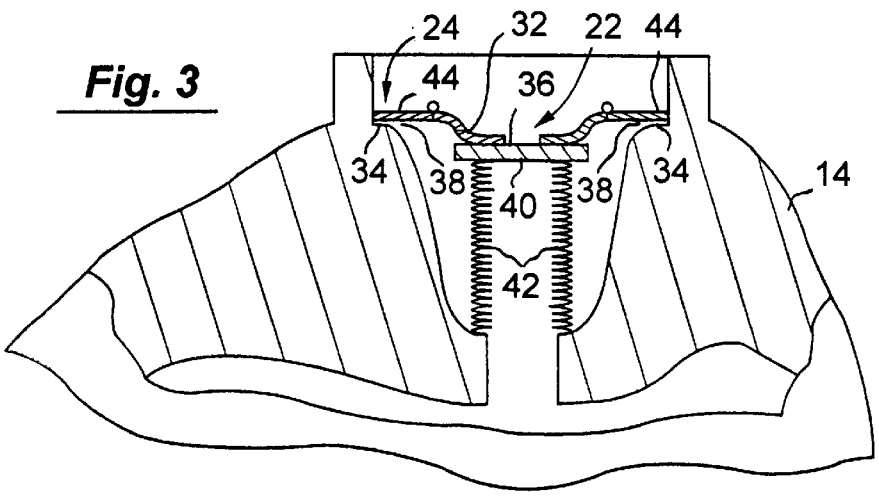
FIG. 3 is a partial cut-away side-view of the facial mask of FIG. 1 having an inspiratory threshold valve which is biased in a closed position.
Figure 4:
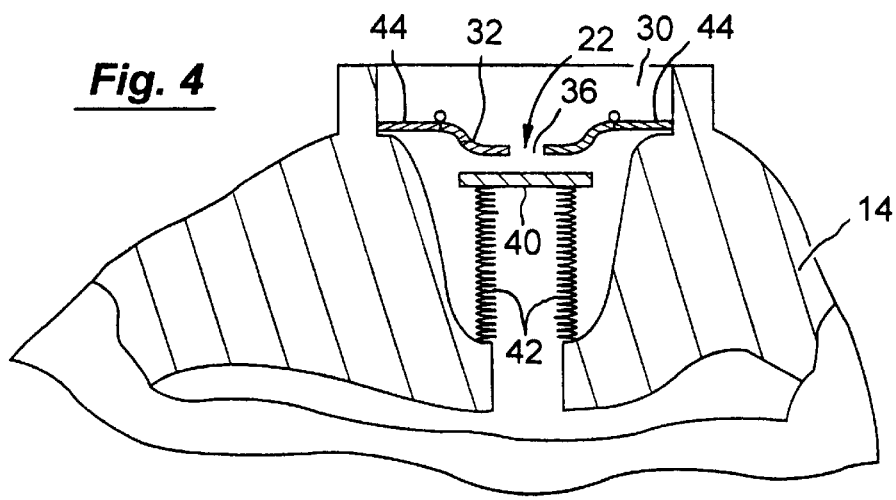
FIG. 4 illustrates the facial mask of FIG. 3 with the inspiratory threshold valve being opened to allow respiratory gasses to flow into the mask.
Figure 5:
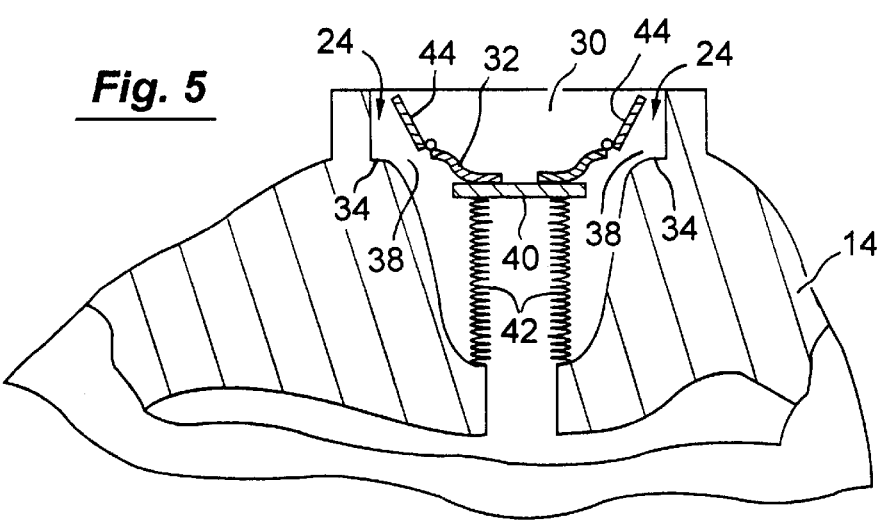
FIG. 5 illustrates the mask of FIG. 3 with the inspiratory threshold valve being closed and a pair of exhalation valves being opened during exhalation of the patient to allow respiratory gasses to exit the mask.

Referring now to FIGS. 3–5, operation of airflow controller 20 will be described in greater detail. As shown in FIG. 3, body 14 includes an opening 30 into which airflow controller 20 is received. A plate 32 (see also FIG. 2) is inserted into opening 30 and rests upon a ridge 34 which is formed in body 14. Plate 32 includes an inflow hole 36 and a pair of outflow holes 38. Holes 36 and 38 are provided for allowing respiratory gasses to flow into and out from mask 12 when valves 22 and 24, respectively, are opened.

Inspiratory threshold valve 22 comprises a seat 40 and a pair of springs 42 (or other biasing members) which are connected at one end to seat 40 and at the other end to body 14. Springs 42 are configured so that seat 40 will remain biased against plate 32 to prevent air from flowing through inflow hole 36 until the specified intrathoracic pressure has developed within the mask.

As shown in FIG. 4, when the specified negative intrathoracic pressure is reached or exceeded, springs 42 compress to unseat seat 40 from plate 32. In this manner, respiratory gasses are allowed to flow through inflow hole 36 and into the patient's lungs. Air will flow into the lungs until springs 42 are able to once again decompress and seat seat 40 against plate 32.

Referring back to FIG. 3, exhalation valves 24 comprise flaps 44 which are pivotally attached at one end to plate 32. In this manner, exhalation valves 26 are configured to be one-way valves, allowing air to only flow from the patient.

As best shown in FIG. 5, when the patient exhales, flaps 44 pivot away from ridge 34 to allow air to flow substantially unimpeded from the patient into the surrounding atmosphere. As the patient begins to inhale, flaps 44 close against ridge 34 and all respiratory gasses are prevented from entering into mask 12 until the specified negative intrathoracic pressure is obtained, whereupon threshold valve 22 opens as previously described.

Figure 6:
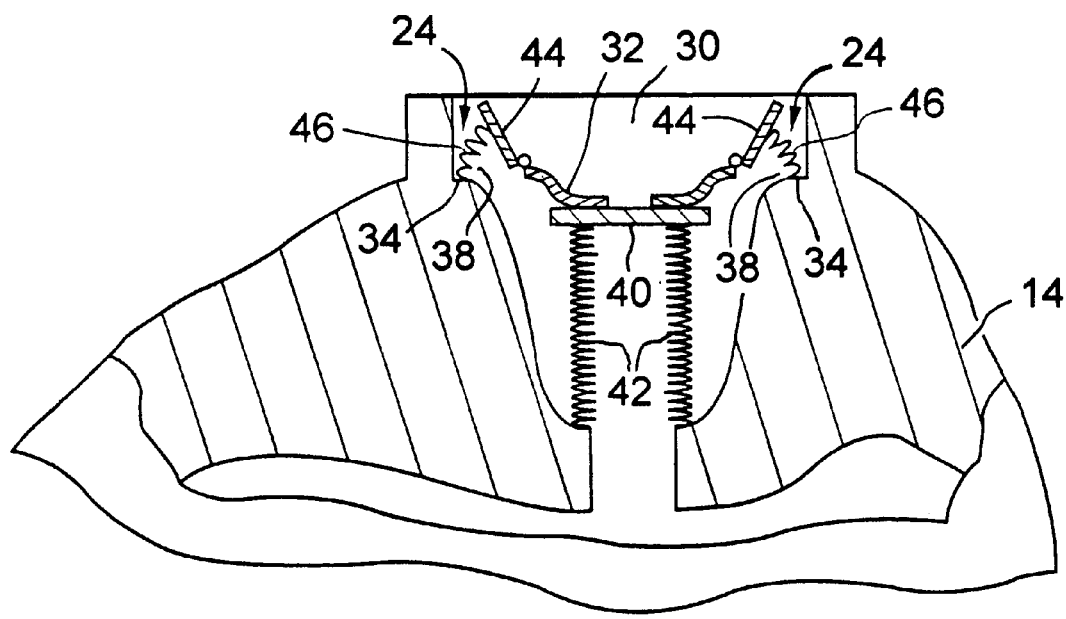
FIG. 6 illustrates the mask of FIG. 5 with biasing members attached to the exhalation valves to provide a pair of expiration threshold valves.

As illustrated in FIG. 6, device 10 may optionally be modified so that flaps 44 function as threshold exhalation valves to increase the extent and duration of positive intrathoracic pressure during exhalation. This is accomplished by providing a pair of springs 46 (or other biasing members) between flaps 44 and ridge 34. Springs 46 are configured such that flaps 44 will not open during exhalation until a threshold positive intrathoracic pressure is reached. Springs 44 will preferably be configured to hold flaps 44 closed until a positive intrathoracic pressure that is in the range from about 3 cm $H_2O$ to about 25 cm $H_2O$ and more preferably from about 5 cm $H_2O$ to about 10 cm $H_2O$ is reached. At that point, flaps 44 open to allow the patient to freely exhale.

Use of such a threshold exhalation valve is particularly advantageous when used with patients suffering from heart failure in an intensive care unit setting in an effort to prevent pulmonary atelectasis. The threshold exhalation valves are also useful in decreasing the chance of pulmonary edema formation.

Although the invention has been described in some detail for purposes of clarity of understanding, it will be appreciated that certain changes and modifications may be made. For example, the number of threshold valves 22 and exhalation valves 24 may be varied depending upon the particular application. Further, alternative mechanical devices may be employed to prevent the flow of gasses to the patient's lungs until a specified intrathoracic pressure is developed within a patient. For example, several exemplary threshold impedance valves and other similar devices are described in U.S. Pat. No. 5,551,420, and co-pending U.S. application Ser. No. 08/403,009, filed Mar. 10, 1995, the complete disclosures of which are herein incorporated by reference.

Figure 7:
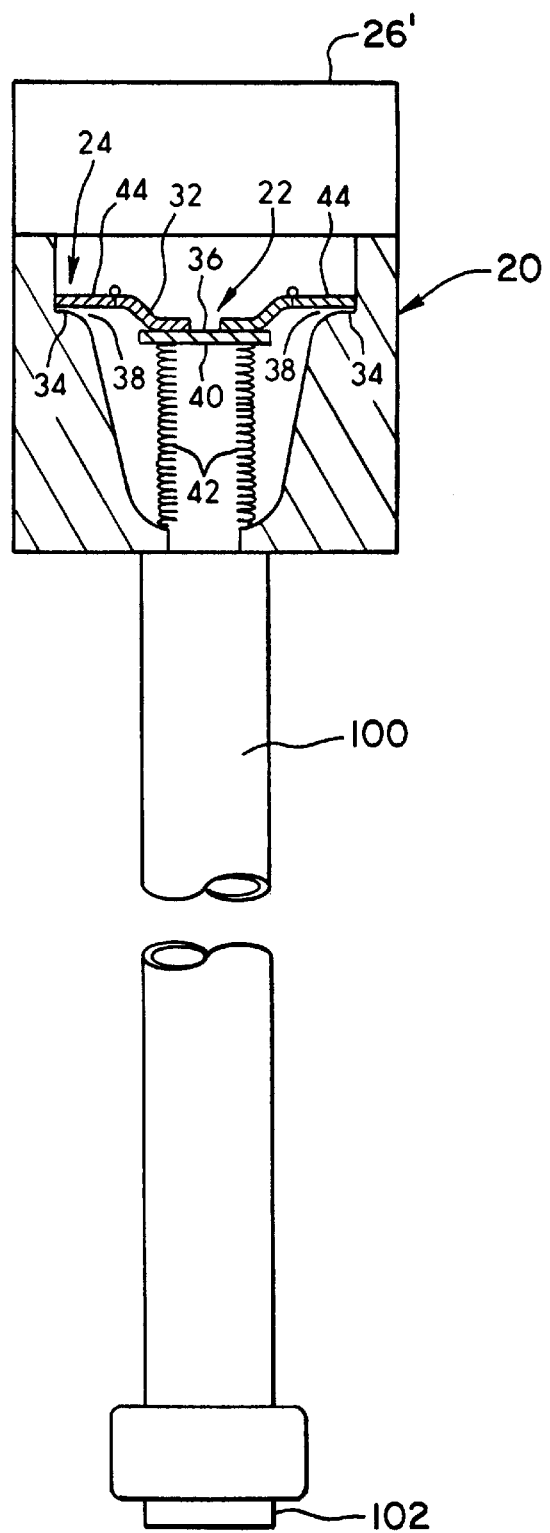
FIG. 7 illustrates an exemplary endotracheal tube having an airflow controller of the mask of FIG. 1.

As another example, airflow controller 20 may be incorporated into an endotracheal tube 100 as illustrated in FIG. 7. With such an arrangement, a distal end 102 of tube 100 is inserted into the patient's airway. Operation of airflow controller 20 proceeds in a manner similar to that previously described. Endotracheal tube 100 may also include a backup inspiratory threshold valve 26' similar to valve 26 of FIG. 2.

What is claimed is:

1. A method for treating a patient suffering from heart failure, the method comprising:

sealing a facial mask around the patient's mouth and nose, the mask including a one-way expiration valve and an inspiratory threshold valve which is biased to open when a threshold pressure within the mask is in the range from about −3 cm $H_2O$ to about −25 cm $H_2O$;

the patient breathing while the mask is sealed to the face, wherein respiratory gases are substantially completely prevented from entering the patient's lungs during inhalation until such time as the patient produces a pressure within the mask that is in the range from about −3 cm H$_2$O to about −25 cm H$_2$O, whereupon the inspiratory valve opens to allow respiratory gases into the lungs; and mechanically altering the negative intrathoracic pressure of the patient.

2. A method as in claim 1, wherein the negative intrathoracic pressure is mechanically altered by placing the patient in an iron lung device or by placing a vest around the patient's chest.

3. A method as in claim 1, wherein during exhalation the exhaled respiratory gases pass through the expiration valve without substantial resistance.

4. A method as in claim 1, wherein the seal is sufficient to maintain a pressure gradient between the pressure outside the mask and the pressure within the mask of at least +20 cm H$_2$O.

5. A method as in claim 1, wherein the mask further includes a port, and further comprising introducing a gas into the port.

6. A method as in claim 1, wherein the mask further includes a back-up inspiratory threshold valve which is biased to open when a threshold pressure within the mask is about 10% to about 100% greater than the threshold pressure of the other threshold valve.

7. A method as in claim 6, further comprising a whistle which produces an audible signal when respiratory gases flow through the back-up threshold valve.

8. A method as in claim 1, wherein the sealing step further comprises strapping the mask to the patient's face.

9. A method as in claim 1, further comprising allowing the patient to breath spontaneously or periodically supplying ventilation to the patient.

10. A method for treating a patient that is suffering from heart failure, the method comprising:

sealing a facial mask around the patients mouth and nose, the mask including a one-way expiration valve and an inspiratory threshold valve which is biased to open when a threshold pressure within the mask is in the range from about −3 cm H$_2$O to about −25 cm H$_2$O;

the patient breathing while the mask is sealed to the face, wherein respiratory gases are substantially completely prevented from entering the patient's lungs during inhalation for a time sufficient to allow a negative intrathoracic pressure that is in the range from about −3 cm H$_2$O to about −25 cm H$_2$O to develop within the patient, whereupon the inspiratory valve opens to allow respiratory gases into the lungs; and periodically ventilating the patient.

11. A method as in claim 10, wherein during exhalation the exhaled respiratory gases pass through the expiration valve without substantial resistance.

12. A method as in claim 10, wherein the seal is sufficient to maintain a pressure gradient between the pressure outside the mask and the pressure within the mask of at least 20 cm H$_2$O.

13. A method as in claim 10, wherein the mask further includes a port, and further comprising ventilating the patient through the port.

14. A method as in claim 10, wherein the mask further includes a back-up inspiratory threshold valve which is biased to open when a threshold pressure within the mask is about 10% to about 100% greater than the threshold pressure of the other threshold valve.

15. A method as in claim 14, further comprising a whistle which produces an audible signal when respiratory gases flow through the back-up threshold valve.

16. A method as in claim 10, wherein the sealing step further comprises strapping the mask to the patient's face.

17. A method as in claim 10, wherein the sealing step further comprises placing an adhesive between the mask and the patient's face.

18. A method for treating a patient suffering from heart failure, the method comprising:

during normal breathing of the patient, preventing respiratory gases from entering the patient's lungs until a negative intrathoracic pressure that is in the range from about −3 cm H$_2$O to about −25 cm H$_2$O is developed within the patient and then allowing respiratory gases to flow into the lungs; and periodically ventilating the patient.

19. A method as in claim 18, further comprising repeating the step of preventing respiratory gases from entering the patient's lungs each time the patient inhales.

20. A device for treating a patient suffering from heart failure, the device comprising:

an endotracheal tube comprising an elongate body which is insertable into a patient's airway, the tube further including a one-way expiration valve and an inspiratory threshold valve which is biased to open when a threshold pressure within the endotracheal tube is in the range from about −3 cm H$_2$O to about −25 cm H$_2$O.

21. A device as in claim 20, wherein the exhalation valve allows the exhaled respiratory gases to pass therethrough without substantial resistance.

22. A device as in claim 20, wherein the endotracheal tube further includes a back-up inspiratory threshold valve which is biased to open when a threshold pressure within the endotracheal tube is about 10% to about 100% greater than the threshold pressure of the other threshold valve.

23. A device as in claim 22, further comprising a whistle which produces an audible signal when respiratory gases flow through the back-up threshold valve.

* * * * *